United States Patent [19]

Lauer et al.

[11] 4,113,384

[45] Sep. 12, 1978

[54] VISCOSITY MEASURING SYSTEM

[75] Inventors: James L. Lauer, Penn Wynne; Melvin E. Peterkin, Brookhaven, both of Pa.

[73] Assignee: Suntech, Inc., Wayne, Pa.

[21] Appl. No.: 791,089

[22] Filed: Apr. 26, 1977

[51] Int. Cl.² ............................................. G01N 33/28
[52] U.S. Cl. ........................................ 356/70; 356/85; 250/459; 73/64
[58] Field of Search .................. 250/458, 459; 356/70, 356/75, 85, 244, 246; 73/54, 64

[56] References Cited

U.S. PATENT DOCUMENTS

| 3,526,127 | 9/1970 | Sarkis | 356/70 X |
| 4,009,962 | 1/1977 | Lauer et al. | 356/70 X |

OTHER PUBLICATIONS

Hawke et al., *Review of Scientific Instruments*, vol. 45, No. 12, Dec. 1974, pp. 1958-1601.
Weinstein et al. *Physical Review B (Solid State)*, vol. 12, No. 4, Aug. 1975, pp. 1172-1186.

*Primary Examiner*—F. L. Evans
*Attorney, Agent, or Firm*—J. Edward Hess; Donald R. Johnson; Paul Lipsitz

[57] ABSTRACT

A method for measuring the viscosity of a lubricant fluid under very high pressures by placing a sample of lubricant containing one or more ruby crystals ($\sim 10\mu m$ diameter) in a diamond anvil cell illuminated with a point source of visible light radiation, and observing by means of appropriate optics the rate of change of band width of the ruby emission spectra at given temperatures and pressures as a measure of the viscosity of the fluid.

3 Claims, 3 Drawing Figures

VISCOSITY MEASURING SYSTEM

The measurement of the viscosity of lubricants under very high pressures is of importance in study of lubrication effects in use. In ball, roller and other type bearings, for example, the lubricant is subjected to extremely high pressures and it is important to determine viscosity changes which might occur to the lubricant. The present invention provides a method for measuring viscosity changes to lubricants under extremely high pressure conditions and thus provides a useful tool for lubricant study.

It is known in the art to use diamond anvil cells for spectroscopic studies at very high pressures on both liquids and solids because of small size, easy and safe operation, and in view of the transparency of diamond throughout most of the electromagnetic spectrum. Piermarini, Block and Barnett (J. Appl. Physics, 46, 2774; 1975) have used such a system for determining the hydrostatic properties of methanol, isopropanol, water, sodium chloride, silver chloride and binary mixtures of pentane-isopentane and methanol-ethanol. In such systems the liquid samples are contained in a hole of a thin metal gasket separating the diamond faces which are squeezed against each other. The liquid sample contains one or more small (about 10 $\mu$m) ruby crystals and the line-broadening and line-shift of the sharp ruby fluorescence line is measured under pressures up to 180 kbar.

It has now been found that by placing a lubricant in the diamond anvil and observing the time rate of change of the band width of the ruby emission spectra at given pressures, the viscosity of the lubricant may be measured at extremely high pressures.

Reference is now made to the drawings to further describe the invention.

Figure 1:
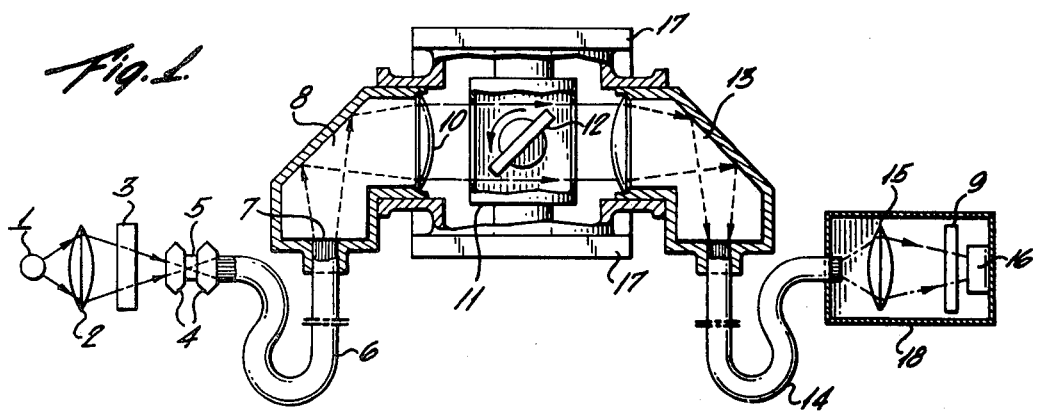
FIG. 1 shows a top view of the optical layout for the system.

Referring now to FIG. 1, a strong light source 1 is needed to excite the fluoroescence of one or more small (~10$\mu$m diameter) ruby crystals. A standard concentrated zirconium arc of the kind used in motion picture projection is adequate. A cadmium-helium laser is more powerful and may be used, but its high expense is not warranted. Since the zirconium arc gives off continuous radiation, a blue filter 3 should follow the condensing lens 2 to avoid overlap with the red ruby fluorescence. A 2 cm pathlength concentrated copper sulfate solution works well as a filter and has the additional advantage of heat removal when placed in front of the condensing lens 2. The quality of this lens is important, for the exciting radiation must be focused precisely within the diamond anvil cell (DAC) cavity 5 between the diamond squeezers 4. An adjustable wide-angle camera lens of 28 mm focal length is a good compromise. The DAC is mounted on a vertically-placed microscope mechanical stage. With this arrangement it is easy to relocate the sample every time a new measurement is to be made.

Flexibility in the optical arrangement is provided on the exit side of the DAC by using the polished ends of an optical fiber bundle 6, one end being pressed against the exit side of the diamond sandwich while the other end is located in the focal plane of a first collimator 8 having high-throughput (f/2) optics.

A key optical element is a tiltable interference filter 12 contained in a thermostatted housing 11. The filter is the usual Fabry-Perot sandwich in the form of a 50 mm diameter disc. By multiple coating, it is possible to achieve a half-bandwidth of 1.9 A for normal incidence of 6976.5 A radiation at 25° C. For scanning, it can be rotated about an axis at its center, which is perpendicular to the plane of the figure. The housing 11 is closed by two windows which also serve as blocking filters for the higher-order passbands of the interference filter.

Another optical fiber bundle 14 leads from a second exit collimator 13 — analogous to a spectrometer telescope — to the photomultiplier housing 18. The far end of the optical fiber bundle is imaged by a lens 15 on the photosensitive surface of the detector. Another interference filter 9 is one of rather wide bandwidth (100 A) and serves to limit the wavelength range accepted by the detector.

Alignment of the optics is simple. The reticles at the focal planes of the collimators are replaced by ground glass plates and ends of the fiber bundles are contacted with them at the location previously occupied by the reticle hole (0.1 mm diameter). The opposite fiber ends are illuminated and the filter 12 is turned until the reflected beams coincide with the fiber bundle ends on the focal planes. This procedure establishes perpendicular incidence on the filter in one plane. The collimators 8 and 13 are aligned with respect to the filter by adjustment of holding screws (not shown) provided in the cylindrical support 17. This support is a heavy-walled steel cylinder to provide rigidity for the system.

The other parts of the optics are adjusted for maximum electronic signal level.

Optionally, but desirably, radiation from a neon and argon source is introduced into the optical train simultaneously with the fluorescence to be used as internal standards for wave length measurements. This is easily done by a beamsplitter (not shown) introducing the neon and/or argon radiation between the filter 3 and the diamond cell 4.

The electrical and electronic system for the apparatus is straight forward. The zirconium arc will have its own special power supply complete with a high-voltage coil for starting. This arc is very bright, stable, long-lived (over 200 hours) and approximates a point source, characteristics which are ideal for the purposes of this method.

The photomultiplier detector is of the end-on type and is employed in conjunction with a shielded housing containing all the dropping resistors, and a stable high-voltage power supply. It is used without cooling. The photomultiplier output is conducted first into a very high impedance electrometer whose output, in turn, is brought to the Y-terminal of an X/Y strip-chart recorder paralleled by a digital voltmeter/paper-tape punch assembly. The recorder is equipped with a precision, "transmitting" potentiometer, whose shaft is mechanically linked to that of the potentiometer varying the X-ramp voltage. The "transmitting" potentiometer is wired as a voltage divider for a low-voltage power supply so that the voltage "transmitted" is proportional to the X-position of the recorder pen. By applying this voltage to the driver unit of a galvanometer suspension attached to the tiltable interference filter, it is possible to interlock the tilt angle with the X-position of the recorder. In this way plots of tilt angle, i.e. X-displacement, can be recorded versus detector signal.

Sometimes it is convenient to substitute manual for electronic scanning. This is done easily by moving the X-zero adjustment of the recorder.

By means of the digital voltmeter/paper-tape punch the amplified detector signal potentials can be recorded in terms of 16-bit numbers at equal increments of tilt angle. A normal scan of the 6930 to 6970 A region contains about 400 points or one point for every 0.1 A. This is approximate because the wavelength scale is non-linear.

Both the diamond anvil cell and the interference filter housing have independent temperature controls.

In carrying out the process, the lubricant to be studied will be placed in the diamond anvil cell together with one or more ruby crystals having a diameter of about 10μm, although size and number of the crystals is not important. The zirconium lamp radiation is taken through the copper sulfate filter to the contents of the diamond cell and the red fluorescence of the ruby crystals conducted by the light-fiber bundle to the focal plane of the collimator 8 ahead of the interference filter housing 11. The radiation passed by the filter is brought by collimator 13 and fiber bundle 14 to the photomultiplier tube housing where a simple lens distributes the radiation on the photocathode. The interference filter 12 1 of wide bandwidth ahead of the detector serves as blocking filter and as a shield against stray radiation.

Radiation from the 6965.43A line of argon and the 6929.47A line of neon are also, desirably, introduced from arc lamps into the radiation train by a beamsplitter ahead of the diamond cell to serve as wavelength markers.

The detector signal is amplified and brought both to the Y-terminal of an X/Y recorder and to the signal terminal of a digital voltmeter (triggered from a clock circuit) whose output is recorded on punched paper tape. The X-ramp voltage of the recorder also drives the scanner (galvanometer head), which rotates the interference filter through a proportional angle.

Figure 2:
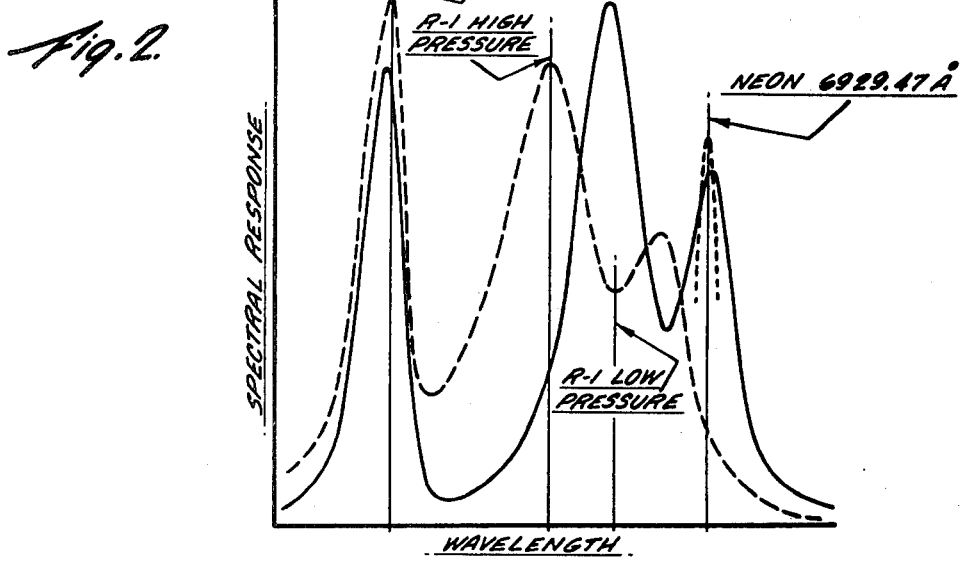
FIG. 2 is a plot showing the spectral scans of the system.

FIG. 2 shows typical recorder traces for the two pressures, containing both the two ruby bands (R-1 and R-2) and the A and Ne lines. The separation of these overlapping features is accomplished by fitting the numerical data to Gaussian bandshapes by computer processing. In this way peak positions and bandwidths are obtained automatically. Pressures are calculated from the R-1 bandpeak shifts, after taking account of the temperatures.

Figure 3:
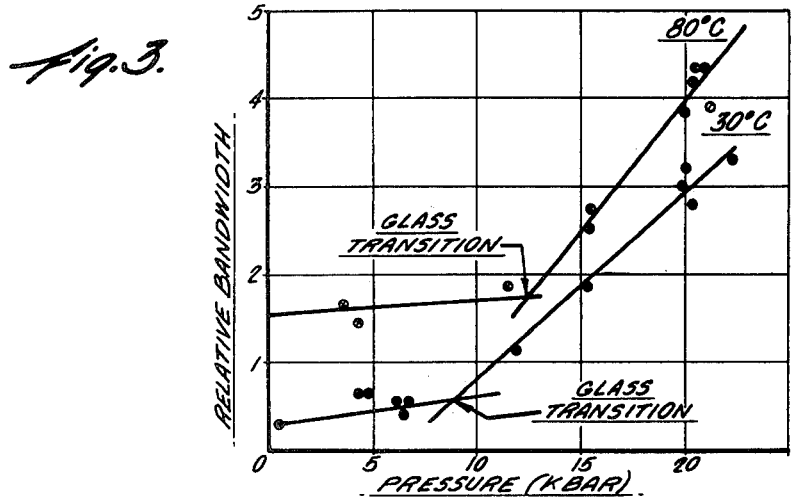
FIG. 3 is a plot to show glass transition pressure changes with temperature.

Glass transition pressures are determined from the knees (e.g. change in slope) on plots, such as FIG. 3, which refers to a typical lubricant. The accuracy of the pressures, as can be seen, is about 0.5 kbar, in the range of 1–75 kbar and 0°–150° C.

FIG. 3 also shows that the glass transition pressures increase with temperature. For practically all hydrocarbons the shift is nearly linear at 13.5° C./kbar in the 10–20 kbar range, which is less than the usual 17° C./kbar near ambient pressures. There is thus a bend in the glass transition temperature/pressure curves. Its significance is not yet clear.

The procedure of determining viscosity ($\eta$) from the change of the width at half-height of the R-1 fluorescence band of ruby depends upon the rate of change of width being proportional to the pressure gradient to which the ruby crystal is subjected. The pressure gradient is, in turn, directly proportional to difference between the actual bandwidth at time $t$ and the final equilibrium bandwidth at infinite time. Calling the bandwidth difference $\Delta\omega$, we therefore have:

$$-\frac{d(\Delta\omega)}{dt} = k\eta^{-1}(\Delta\omega) = \frac{k}{\eta}(\Delta\omega) \tag{1}$$

In other words, the rate change of bandwidth is proportional to the excess bandwidth, the minus sign being required because the excess bandwidth decreases with time. Here $k$ is a apparatus constant and $\eta$ is the viscosity. Note that the rate change is smaller, the larger the viscosity.

Equation (1) is the familiar first order rate equation. Integrated, it becomes:

$$\Delta\omega = e^{-kt/\eta}$$

or $$ln(\Delta\omega) = -kt/72 \tag{2}$$

A convenient way of finding $(k/\eta)$ is by determining the time $t_{\frac{1}{2}}$ at which $\Delta\omega$ has dwindled to half its initial value.

$$\frac{k}{\eta} \alpha \frac{1}{t_{1/2}} \text{ or } \eta = k' \, t_{1/2} \tag{3}$$

where $k'$ is a newly defined apparatus constant.

In practice $k'$ is eliminated by calibration with a fluid of known viscosity.

In a more specific illustration, assume that it takes 1000 seconds for glycerine in the diamond anvil cell at 10 kbar of pressure to produce a ruby band whose excess R-1 fluorescence bandwidth has decreased to half of its original value. At this pressure, the viscosity of glycerine is known to be 100 poise. Then $k' = 100/1000 = 0.1$. If we then have a liquid at the same pressure, which requires 10,000 seconds for the excess bandwidth to decline to half its value, we know that its viscosity is directly proportional to that of glycerine at 10 kbar and thus the viscosity of the sample is ten time that of glycerine. The same ruby crystal, of course, must be used in both measurements, since its geometry determines the rate of change of bandwidth.

Generally, hours or days are required to determine $t_{\frac{1}{2}}$ since the viscosities of liquids under pressure can reach up to $10^{13}$ poise, when the liquid has become a glass.

In order to further illustrate the invention the following example is given:

EXAMPLE

A sample of lubricating oil in the diamond anvil cell was pressured to 10 kbar and the bandwidth at half-height of the R-1 ruby fluorescence spectra was 20.7 A. Observations were made over a two month period to determine changes of bandwidth with time and until there was no change; the final bandwidth being 15.2 A. The pertinent data follows:

| Time (sec.) | Bandwidth Increase ($\Delta\omega$ in A) |
|---|---|
| 0 | 5.5 |
| 1 × 10⁵ | 4.9 |
| 3 × 10⁵ | 4.1 |
| 5 × 10⁵ | 3.4 |
| 7 × 10⁵ | 2.7 |
| 1 × 10⁶ | 2.0 |
| 2 × 10⁶ | 2.7 |

| Time (sec.) | Bandwidth Increase (Δω in A) |
|---|---|
| 5 × 10⁶ | 0.0 |

The above data shows that the bandwidth increase was halved after $7 \times 10^5$ seconds. It had been earlier determined that the same ruby crystal gave a 50% bandwidth decline after $1 \times 10^3$ seconds for glycerine in the same cell and at the same pressure. The viscosity of glycerine under those conditions was 100 poise. Since the time for half bandwidth decline for the lubricating oil sample is 700 times longer, the viscosity of the oil at 10 kbar is $700 \times 100 = 7 \times 10^4$ poise.

Thus in simple mathematical terms, the viscosity of the lubricant sample ($\eta$) is given as:

$$\eta = \frac{\eta' \times t'_{1/2}}{t_{1/2}}$$

where $\eta'$ is the viscosity of the standard (e.g. glycerine), $t_{\frac{1}{2}}$ is the time required for the width at half-height of the ruby R-1 fluorescence band of the lubricant to decline to half its initial value and $t'_{\frac{1}{2}}$ is the time for the width at half-height of R-1 band of the standard to decline to half its original value.

The invention claimed is:

1. A method for measuring the viscosity of a lubricant fluid under very high pressures by placing a sample of lubricant contaning one or more rube crystals in a diamond anvil cell illuminated with a point source of visible light radiation, observing the rate of change of the width at half-height of the $R_1$ fluorescence band of the ruby emission spectra at given temperatures and pressures and correlating said change with an empirical calibration of a fluid of known viscosity under the same conditions.

2. The method of claim 1 where the visible light source is a zirconium arc filtered to remove blue radiation.

3. The method of claim 2 wherein the ruby crystals will have a diameter of about 10 μm.

* * * * *